United States Patent [19]

Baader et al.

[11] Patent Number: 5,204,338

[45] Date of Patent: Apr. 20, 1993

[54] OXALYLAMINO ACID DERIVATIVES AND THEIR USE AS MEDICAMENTS FOR INHIBITING PROLINE HYDROXYLASE

[75] Inventors: Ekkehard Baader, Königstein; Harald Burghard, Schmitten; Volkmar Günzler-Pukall, Marburg, all of Fed. Rep. of Germany

[73] Assignee: Hoechst Aktiengesellschaft, Frankfurt am Main, Fed. Rep. of Germany

[21] Appl. No.: 698,097

[22] Filed: May 10, 1991

[30] Foreign Application Priority Data

May 12, 1990 [DE] Fed. Rep. of Germany ....... 4015255

[51] Int. Cl.$^5$ ............................................. A61K 31/395
[52] U.S. Cl. ..................................... 514/183; 514/210; 514/423; 514/513; 514/563; 548/953
[58] Field of Search ............... 548/953; 514/183, 210, 514/423, 513, 563

[56] References Cited

U.S. PATENT DOCUMENTS 3,560,516 2/1971 Yoshida ................................ 260/307
3,646,061 2/1972 Maeda ............................. 260/326.14

FOREIGN PATENT DOCUMENTS 1533817 7/1968 France .
2010601 2/1970 France .

OTHER PUBLICATIONS

Mulliez et al, *Tetrahedron*, 40(24), 5143-51, 1984.
Warren, et al, *J. Chromatography*, 64(2), 219-37, 1972.

Chemical Abstracts, vol. 70, No. 3, Jan. 20, 1969, No. 11984.
Chemical Abstracts, vol. 77, No. 19, Nov. 6, 1972, No. 125909z.
Biochemistry, vol. 27, No. 8, Apr. 19, 1988, pp. 2934-2943.
FEBS Letters, vol. 90, No. 2, Jun. 1978, pp. 218-222.

*Primary Examiner*—Joseph Paul Brust
*Assistant Examiner*—Jacqueline Haley
*Attorney, Agent, or Firm*—Finnegan, Henderson, Farabow, Garrett & Dunner

[57] ABSTRACT

The invention relates to oxalylamino acid derivatives of the formula I

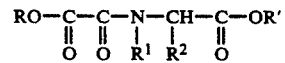

in which
R and R' are identical or different and are $C_1$-$C_6$-alkyl or hydrogen,
$R^1$ is hydrogen or $C_1$-$C_4$-alkyl,
$R^2$ is hydrogen, $C_1$-$C_6$-alkyl, $C_1$-$C_3$-alkoxy, carboxyl, $C_1$-$C_6$-alkoxycarbonyl, aryl, SH, $NH_2$ or halogen, where the alkyl radicals are unsubstituted or substituted by aryl, OH, SH or $NH_2$
or
$R^1$ and $R^2$ together are a $C_2$-$C_4$-alkylene chain and the compounds in their predominantly pure D- and L-form and the physiologically tolerable salts.

The compounds are distinguished as excellent inhibitors of prolyl hydroxylase and lysine hydroxylase.

12 Claims, No Drawings

OXALYLAMINO ACID DERIVATIVES AND THEIR USE AS MEDICAMENTS FOR INHIBITING PROLINE HYDROXYLASE

Oxalylamino acid derivatives are known and described, for example, in FR-A 2,010,601, JP 43/10614 or Biochemistry, 27 (8), 2934–2943 (1988). However, a use of these compounds as medicaments is not described in the prior art.

It has now been found that oxalylamino acid derivatives of the formula I

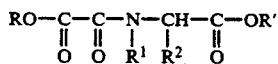

in which

R and R' are identical or different and are $C_1$–$C_6$-alkyl or hydrogen, $R^1$ is hydrogen or $C_1$–$C_4$-alkyl, $R^2$ is hydrogen, $C_1$–$C_6$-alkyl, $C_1$–$C_3$-alkoxy, carboxyl, $C_1$–$C_6$-alkoxycarbonyl, aryl, SH, $NH_2$ or halogen, where the alkyl radicals are unsubstituted or substituted by aryl, OH, SH or $NH_2$ or $R^1$ and $R^2$ together are a $C_2$–$C_4$-alkylene chain and the compounds in their predominantly pure D- and L-form and the physiologically tolerable salts are excellent inhibitors of proline hydroxylase and lysine hydroxylase.

The invention thus relates to the use of the abovementioned compounds as medicaments, in particular as medicaments for influencing the metabolism of collagen and collagen-like substances.

The invention relates in particular to the use of those compounds of the formula I in which R and R' are identical or different and are $C_1$–$C_3$-alkyl, Na or K, $R^1$ is hydrogen, methyl or ethyl, $R^2$ is hydrogen or $C_1$–$C_4$-alkyl, where the alkyl radical is unsubstituted or substituted by phenyl or SH or $R^1$ and $R_2$ together form a $C_2$- or $C_3$-alkylene chain.

The use of compounds of the formula I in which

R and R' are identical and are methyl, ethyl, Na or K, $R^1$ is hydrogen or methyl, $R^2$ is hydrogen, $C_1$–$C_3$-alkyl, benzyl or thiomethyl, or $R^1$ and $R^2$ together form an ethylene chain, is very particularly preferred.

Alkyl chains having 3 and more carbon atoms can be both straight-chain and branched. Aryl is understood as meaning aromatic hydrocarbons, in particular phenyl and naphthyl. Halogen is understood as meaning fluorine, chlorine, bromine and iodine, in particular chlorine and bromine.

The preparation of compounds of the formula I is known and described, for example, in FR-A 2,010,601. It is carried out most simply by combining 1-3 equivalents of amino acid ester hydrohalide, preferably hydrochloride, and 1-5 equivalents of a base such as, for example, carbonate or hydrogencarbonate, such as sodium carbonate or potassium carbonate or sodium hydrogencarbonate or potassium hydrogencarbonate or tertiary amines, such as triethylamine, tributylamine, ethyldiisopropylamine or heterocyclic amines such as N-alkylmorpholine, pyridine, quinoline or dialkylanilines.

If desired, a plurality of bases can also be employed simultaneously. The reaction temperatures are −30° C. to 150° C., preferably 20° C. to 100° C. If desired, the reaction can also be carried out in a solvent, such as diethyl ether or dimethoxyethane or tetrahydrofuran, chlorinated hydrocarbons such as methylene chloride, chloroform, tri- or tetrachloroethylene, benzene, toluene and also polar solvents such as dimethylformamide, acetone, alcohols such as methanol or ethanol or dimethyl sulfoxide. 1-3 equivalents of oxalic acid ester chloride are then added slowly at temperatures between −78° C. and 100° C., preferably between −20° C. and +20° C. If desired, the reaction here can also be carried out using a solvent such as the abovementioned. The completion of the reaction can be determined, for example, by means of thin layer chromatography.

If desired, the working up of the products can be carried out, for example, by extraction or by chromatography, for example on silica gel. The isolated product can be recrystallized.

Compounds of the formula I where R and/or R'=alkali metal such as, for example, Na or K can be prepared, for example, from the corresponding compounds of the formula I where R and/or R'=$C_1$–$C_4$-alkoxy by hydrolysis in alkaline medium, for example using NaOH or KOH in a low molecular weight alcohol such as methanol or ethanol or in ethers such as dimethoxyethane or tetrahydrofuran, if desired in the presence of water. The alkali metal cation in the salts obtained can be replaced by any desired cations by acidifying in ion exchangers in the customary manner. To do this, the acids, for example, are allowed to run through a column filled with a cation exchanger, such as, for example, one based on polystyrene/divinylbenzene (®Amberlite CG-150 or ®Dowex-CCR-2). The cation exchanger is loaded with the desired cation, for example with ammonium ions which are derived from a primary, secondary or tertiary amine. The desired salt is obtained by evaporating the eluate.

Ammonium salts of the acids which are derived from a primary, secondary or tertiary amine can also be prepared by adding an equimolar amount of the appropriate amine to the free acids in an alcoholic solution and evaporating the solvent.

The preparation of the predominantly enantiomerically pure D- or L-compounds from the racemates is likewise carried out by methods known from the literature, for example by fractional crystallization or by enzymatic work-up. Another possibility comprises the direct synthesis of the enantiomerically pure compound from appropriate D- or L-precursors (starting compounds).

The substances according to the invention are effective as reversible inhibitors of prolyl hydroxylase. As a result, they cause selective inhibition of the collagen-specific hydroxylation reaction, in the course of which protein-bound proline is hydroxylated by the enzyme prolyl hydroxylase. On suppressing this reaction by means of an inhibitor, an underhydroxylated collagen molecule which is incapable of functioning is formed, which can be released by the cell into the extracellular space only to a small extent. The underhydroxylated collagen can additionally not be incorporated into the collagen matrix and is very easily degraded proteolytically. As a consequence of these effects, the amount of extracellularly deposited collagen is reduced in total. Inhibitors of prolyl hydroxylase are therefore suitable tools in the treatment of disorders in which the deposition of collagens contributes significantly to the syndrome. These include, inter alia, fibroses of the lungs, liver and skin (scleroderma) and atherosclerosis.

It is additionally known that the inhibition of proline hydroxylase by known inhibitors such as α, α-dipyridyl leads to an inhibition of Clq biosynthesis of macrophages (W. Müller et al., FEBS Lett. 90, 218 et seq. (1978)). A failure of the classical route of complement activation occurs as a result; inhibitors of prolyl hydroxylase therefore also act as immunosuppressives, for example in immune complex diseases.

The substances according to the invention can therefore be employed as fibrosuppressives, immunosuppressives and antiatherosclerotics.

The antifibrotic activity can be determined in the carbon tetrachloride-induced liver fibrosis model. To do this, rats are treated twice weekly with CCl$_4$ (1 ml/kg)—dissolved in olive oil. The test substance is administered daily, if appropriate even twice daily, orally or intraperitoneally—dissolved in a suitable compatible solvent. The extent of liver fibrosis is determined histologically and the proportion of collagen in the liver is analyzed by hydroxylproline determination—as described in Kivirikko et al. (Anal. Biochem. 19, 249 et seq. (1967)). The activity of the fibrogenesis can be determined by radioimmunological determination of collagen fragments and procollagen peptides in the serum. The compounds according to the invention are active in this model in a concentration of 1–100 mg/kg. Another model for the evaluation of the antibiotic activity is the bleomycin-induced lung fibrosis model, as described in Kelley et al. (J. Lab. Clin. Med 96, 954, (1980)). For the evaluation of the activity of the compounds according to the invention in the granulation tissue, the cotton swab granuloma model, as is described in Meier et al., Experimentia 6, 469 (1950), can be used. The invention is illustrated in more detail by examples in the following.

EXAMPLES

General procedure for the preparation of the compounds of Examples 1–6.

One equivalent of amino acid ester hydrochloride, two equivalents of triethylamine and 2 equivalents of N,Ndimethylaminopyridine are initially introduced into methylene chloride at room temperature under a nitrogen atmosphere. One equivalent of oxalic acid ester chloride dissolved in methylene chloride is then slowly added dropwise at 0° C.–10° C. The mixture is stirred at room temperature for 12 hours, saturated sodium hydrogen-carbonate solution is added and the mixture is extracted. The organic phase is separated off, washed with sodium chloride solution, dried with magnesium sulfate and evaporated. The crude product is chromatographed.

EXAMPLE 1

(N-Oxalyl)-L-alanine dimethyl ester

R=R'=CH$_3$; R$^1$=H; R$^2$=CH$_3$ 5 g of L-alanine methyl ester hydrochloride and 3.3 ml of oxalic acid methyl ester chloride give 6 g of Example 1 as an oil (chromatography: EA/CH$_3$OH 5/1)

EXAMPLE 2

(N-Oxalyl)-L-phenylalanine dimethyl ester

R=R'=CH$_3$; R$^1$=H; R$^2$=CH$_2$C$_6$H$_5$ 5 g of L-phenylalanine methyl ester hydrochloride and 2.2 ml of oxalic acid methyl ester chloride give 6.5 g of Example 2 as an oil (chromatography: EA/CH$_3$OH 5/1)

EXAMPLE 3

(N-Oxalyl)-L-glycine dimethyl ester

R=R'=CH$_3$; R$^1$=H; R$^2$=H 15 g of L-glycine methyl ester hydrochloride and 11 ml of oxalic acid monomethyl ester chloride give 23 g of Example 3; m.p. 49° C.; (chromatography: EA)

EXAMPLE 4

(N-Oxalyl)-L-proline dimethyl ester

R=R'=CH$_3$; R$^1$=CH$_2$—CH$_2$=R$^2$ 2 g of L-proline methyl ester hydrochloride and 2.9 g of oxalic acid monomethyl ester chloride give 1.5 g as an oil (chromatography: EA).

EXAMPLE 5

(N-Oxalyl)-L-valine dimethyl ester

R=R'=CH$_3$; R$^1$=H; R$^2$=—CH(CH$_3$)$_2$ 2 g of L-valine methyl ester hydrochloride and 2.8 g of oxalic acid monomethyl ester chloride give 2 g as an oil (chromatography: CH/EA 1/1)

EXAMPLE 6

(N-Oxalyl)-L-cysteine dimethyl ester R=R'=CH$_3$; R$^1$=H; R$^2$=CH$_2$SH 2 g of L-cysteine methyl ester hydrochloride and 3.9 g of oxalic acid monomethyl ester chloride give 1.5 g as an oil (chromatography: CH/EA 1/1)

EXAMPLE 7

(N-Oxalyl)sarcosine diethyl ester R=R'=C$_2$H$_5$; R$^1$=CH$_3$; R$^2$=H

Initially introduce 2 g of sarcosine ethyl ester hydrochloride into 50 ml of ethanol and add a solution of 3.5 ml (2 equivalents) of diethyl oxalate and 1.8 ml of triethylamine in 25 ml of ethanol dropwise at room temperature. Stir at 50° C. for 5 hours, then heat to reflux for 2 hours. The solution is cooled and evaporated to dryness. Take up the residue with methylene chloride, wash once with water, dry the organic phase over magnesium sulfate and evaporate.

The crude product is chromatographed (EA/CH 1/1)

Yield: 0.35 g

General Procedure for the Preparation of the Compounds of Examples 8–14

One equivalent of the compound from Examples 1–7 is dissolved at room temperature using 2 equivalents of 0.1 N alcoholic alkali metal hydroxide solution. The mixture is stirred at room temperature for 12 hours and evaporated to dryness. The residue is evaporated twice with toluene, washed several times with pentane and dried in a high vacuum.

EXAMPLE 8

(N-Oxalyl)-L-alanine dipotassium salt

R=R$^1$=K; R$^1$=H; R$^2$=CH$_3$ 300 mg of the compound from Example 1 are reacted with 32.5 ml of 0.1 N ethanolic potassium hydroxide solution. Yield: 370 mg of white crystals, m.p.:>300° C.

EXAMPLE 9

(N-Oxalyl)-L-phenylalanine disodium salt

R=R²=Na; R¹=H; R²=CH₂C₆H₅

420 mg of the compound from Example 2 are reacted with 32.5 ml of 0.1 N methanolic sodium hydroxide solution.

Yield: 440 mg of white crystals, m.p.:>300° C.

EXAMPLE 10

(N-Oxalyl)-L-glycine dipotassium salt

R=R²=K; R¹=H; R²=H 5.5 g of the compound from Example 3 are reacted with 314 ml of 0.1 N methanolic potassium hydroxide solution.

Yield: 5.4 g of white crystals, m.p.: >300° C.

EXAMPLE 11

(N-Oxalyl)-L-proline disodium salt

R=R¹=Na; R¹=CH₂—CH₂=R²

300 mg of the compound from Example 4 are reacted with 1.5 ml of 0.1 N ethanolic sodium hydroxide solution.

Yield: 290 mg of white crystals, m.p.:>300° C.

EXAMPLE 12

(N-Oxalyl)-L-valine disodium salt

R=R'=Na; R¹=H; R²=CH(CH₃)₂

300 mg of the compound from Example 5 are reacted with 14 ml of 0.1 N ethanolic sodium hydroxide solution.

Yield: 235 mg of white crystals, m.p.:>300° C.

EXAMPLE 13

(N-Oxalyl)-L-cysteine disodium salt

R=R¹=Na; R¹=H; R²=CH₂SH 300 mg of the compound from Example 6 are reacted with 13.7 ml of 0.1 N methanolic sodium hydroxide solution.

Yield: 300 mg of white crystals, m.p.:>300° C.

EXAMPLE 14

(N-Oxalyl)sarcosine dipotassium salt

R=R'=K; R¹=CH₃; R²=H 120 mg of the compound from Example 7 are reacted with 11.4 ml of 0.1 N ethanolic potassium hydroxide solution.

Yield: 130 mg of white crystals, m.p.:>300° C.

The compounds of Examples 1-14 are shown in tabular form below (Table 1)

TABLE 1

$$RO-\underset{O}{\overset{\|}{C}}-\underset{O}{\overset{\|}{C}}-\underset{R^1}{\overset{|}{N}}-\underset{R^2}{\overset{|}{CH}}-\overset{\|}{\underset{O}{C}}-OR'$$

| Example | R | R' | R¹ | R² | M.p./Oil |
|---|---|---|---|---|---|
| 1 | CH₃ | CH₃ | H | CH₃ | Oil |
| 2 | CH₃ | CH₃ | H | CH₂C₆H₅ | Oil |
| 3 | CH₃ | CH₃ | H | H | 49° C. |
| 4 | CH₃ | CH₃ | CH₂— | CH₂ | Oil |
| 5 | CH₃ | CH₃ | H | CH(CH₃)₂ | Oil |
| 6 | CH₃ | CH₃ | H | CH₂SH | Oil |
| 7 | C₂H₅ | C₂H₅ | CH₃ | H | Oil |
| 8 | K | K | H | CH₃ | >300° C. |
| 9 | Na | Na | H | CH₂C₆H₅ | >300° C. |
| 10 | K | K | H | H | >300° C. |
| 11 | Na | Na | CH₂— | CH₂ | >300° C. |

TABLE 1-continued $$RO-\underset{O}{\overset{\|}{C}}-\underset{O}{\overset{\|}{C}}-\underset{R^1}{\overset{|}{N}}-\underset{R^2}{\overset{|}{CH}}-\overset{\|}{\underset{O}{C}}-OR'$$

| Example | R | R' | R¹ | R² | M.p./Oil |
|---|---|---|---|---|---|
| 12 | Na | Na | H | CH(CH₃)₂ | >300° C. |
| 13 | Na | Na | H | CH₂SH | >300° C. |
| 14 | K | K | CH₃ | H | >300° C. |

The inhibitory activity of the compounds according to the invention was determined in an enzyme test similarly to the method of B. Peterkofsky and R. DiBlasio, Anal. Biochem. 66, 279-286 (1975). In this test, underhydroxylated collagen is enzymatically hydroxylated with prolyl hydroxylase in the presence of iron(II) ions, α-keto glutarate and ascorbate, and that concentration of the compound according to the invention added which leads to an 80% inhibition of enzyme activity (the value is indicated as $K_i$) is determined.

In Table 2, the results with the compounds of Examples 8 and 10 are shown.

TABLE 2

(salts):

| Compound | $K_i$[mM] |
|---|---|
| Example 8 | 0.04 |
| Example 10 | 0.01 |

The inhibitory activity can also be determined in cell or tissue culture. To do this, fibroblasts or other collagen-producing cells or calvaria or other collagen-producing organs can be employed. The inhibitory activity of substances according to the invention in calvaria culture is collated in Table 3. The concentration is indicated which leads to a 50% reduction of the hydroxyproline/proline quotients in metabolic labeling with ¹⁴C-proline (IC₅₀).

TABLE 3

(esters):

| Compound | IC₅₀[mM] |
|---|---|
| Example 1 | 0.35 |
| Example 3 | 0.002 |

What is claimed is:

1. A method for influencing the metabolism of collagen and collagen-like substances comprising administering an effective amount of an oxalylamino acid compound or a physiologically tolerable salt thereof, of the formula I

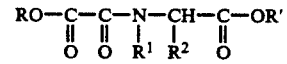

in which

R and R' are identical or different and are C₁-C₆alkyl or hydrogen,

R¹ is hydrogen or C₁-C₄-alkyl,

R² is hydrogen, C₁-C₆-alkyl, C₁-C₃-alkoxy, carboxyl, C₁-C₆-alkoxycarbonyl, aryl, SH, NH₂ or halogen, where the alkyl radicals are unsubstituted or substituted by aryl, OH, SH or NH₂ or

R¹ and R² together are a C₂-C₄-alkylene chain.

2. The method of claim 1, wherein

R and R' are identical or different and are $C_1$-$C_3$-alkyl, Na or K,
$R^1$ is hydrogen, methyl or ethyl,
$R^2$ is hydrogen or $C_1$-$C_4$-alkyl, where the alkyl radical is unsubstituted or substituted by phenyl or SH
or
$R^1$ and $R^2$ together form a $C_2$- or $C_3$-alkylene chain.

3. The method of claim 1, wherein
R and R' are identical and are methyl, ethyl, Na or K,
$R^1$ is hydrogen or methyl,
$R^2$ is hydrogen, $C_1$-$C_3$-alkyl, benzyl or thiomethyl, or
$R^1$ and $R^2$ together form an ethylene chain.

4. The method of claim 1, wherein the compound is in its predominantly pure D-form or L-form.

5. A method for the treatment of disorders of the metabolism of collagen and collagen-like substances comprising administering an effective amount of an oxalylamino acid compound or physiologically tolerable salt thereof, of the formula I

in which
R and R' are identical or different and are $C_1$-$C_6$alkyl or hydrogen,
$R^1$ is hydrogen or $C_1$-$C_4$-alkyl,
$R^2$ is hydrogen, $C_1$-$C_6$-alkyl, $C_1$-$C_3$-alkoxy, carboxyl, $C_1$-$C_6$-alkoxycarbonyl, aryl, SH, $NH_2$ or halogen, where the alkyl radicals are unsubstituted or substituted by aryl, OH, SH or $NH_2$
or
$R^1$ and $R^2$ together are a $C_2$-$C_4$-alkylene chain.

6. The method of claim 5, wherein R and R' are identical or different and are $C_1$-$C_3$alkyl, Na or K,
$R^1$ is hydrogen, methyl or ethyl,
$R^2$ is hydrogen or $C_1$-$C_4$-alkyl, where the alkyl radical is unsubstituted or substituted by phenyl or SH
or
$R^1$ and $R^2$ together form a $C_2$- or $C_3$-alkylene chain.

7. The method of claim 5, wherein
R and R' are identical and are methyl, ethyl, Na or K,
$R^1$ is hydrogen or methyl,
$R^2$ is hydrogen, $C_1$-$C_3$-alkyl, benzyl or thiomethyl, or
$R^1$ and $R^2$ together form an ethylene chain.

8. The method of claim 5, wherein the compound is in its predominantly pure D-form or L-form.

9. A pharmaceutical composition comprising an effective amount of an oxalylamino acid compound or physiologically active salt thereof, of the formula I

in which
R and R' are identical or different and are Na, K or hydrogen,
$R^1$ is $C_1$-$C_4$-alkyl,
$R^2$ is $C_1$-$C_6$-alkyl, $C_1$-$C_3$-alkoxy, carboxyl, $C_1$-$C_6$-alkoxycarbonyl, aryl, SH, $NH_2$ or halogen, where the alkyl radicals are unsubstituted or substituted by aryl, OH, SH or $NH_2$
or
$R^1$ and $R^2$ together are a $C_2$-$C_4$-alkylene chain, in a compatible pharmaceutical carrier.

10. The pharmaceutical composition of claim 9, wherein
R and R' are identical or different and are Na or K,
$R^1$ is methyl or ethyl,
$R^2$ is $C_1$-$C_4$-alkyl, where the alkyl radical is unsubstituted or substituted by phenyl or SH
or
$R^1$ and $R^2$ together form a $C_2$- or $C_3$-alkylene chain.

11. The pharmaceutical composition of claim 9, wherein R and R' are identical and are hydrogen, Na or K,
$R^1$ is methyl,
$R^2$ is $C_1$-$C_3$-alkyl, benzyl or thiomethyl,
or
$R^1$ and $R^2$ together form and ethylene chain.

12. The pharmaceutical composition of claim 9, wherein the compound is in the predominantly pure D-form or L-form.

* * * * *